United States Patent [19]

Mosseri

[11] Patent Number: 5,925,353
[45] Date of Patent: Jul. 20, 1999

US005925353A

[54] TARGETED RADIOIMMUNOTHERAPY

[76] Inventor: Salomon Mosseri, 9 Rue Etex, 75018 Paris, France

[21] Appl. No.: 08/831,387

[22] Filed: Apr. 1, 1997

[51] Int. Cl.⁶ .................. A61K 39/395; A61K 39/40; A61K 39/42; A61K 39/44; A61F 13/00; A61F 2/04; A61N 5/00; A61M 5/00

[52] U.S. Cl. .............. 424/178.1; 435/7.1; 435/283.1; 436/528; 436/529; 436/530; 436/531; 436/532; 436/804; 436/807; 424/179.1; 424/180.1; 424/181.1; 424/1.49; 424/422; 600/1; 600/3; 600/36; 604/101; 606/194; 606/195; 623/1; 623/11; 623/12

[58] Field of Search .............. 600/1, 3, 36; 424/1.49, 424/422, 423, 130.1, 138.1, 178.1, 179.1, 180.1, 181.1; 436/528–532, 804, 807; 435/4, 7.1, 287.1, 287.2, 287.7–283.1, 287.9; 604/109; 606/194, 195; 623/1, 11, 12

[56] References Cited

U.S. PATENT DOCUMENTS 5,131,907  7/1992  Williams et al. .................. 600/36
5,554,182  9/1996  Dinh et al. ....................... 623/1
5,607,475  3/1997  Cahalan et al. .................... 623/11

*Primary Examiner*—Sheela Huff
*Attorney, Agent, or Firm*—Mark M. Friedman

[57] ABSTRACT

A stent for the inhibition of restenosis. The stent is coated with an antigen which can be bound by a labelled antibody. The antibody is preferably labelled with a radioactive source. After the stent has been placed in the blood vessel of the subject, the antibody is injected. The antibody then binds to the antigen on the stent, thereby localizing the radioactive source to the area to be treated, for example for restenosis. Other biomedical devices, such as coil, artificial valve and vascular graft, could also be used in the place of the stent. The biomedical device could be placed in another biological passageway, such as the gastrointestinal tract, an airway or the genitourinary tract.

11 Claims, 4 Drawing Sheets

18
16

18
16

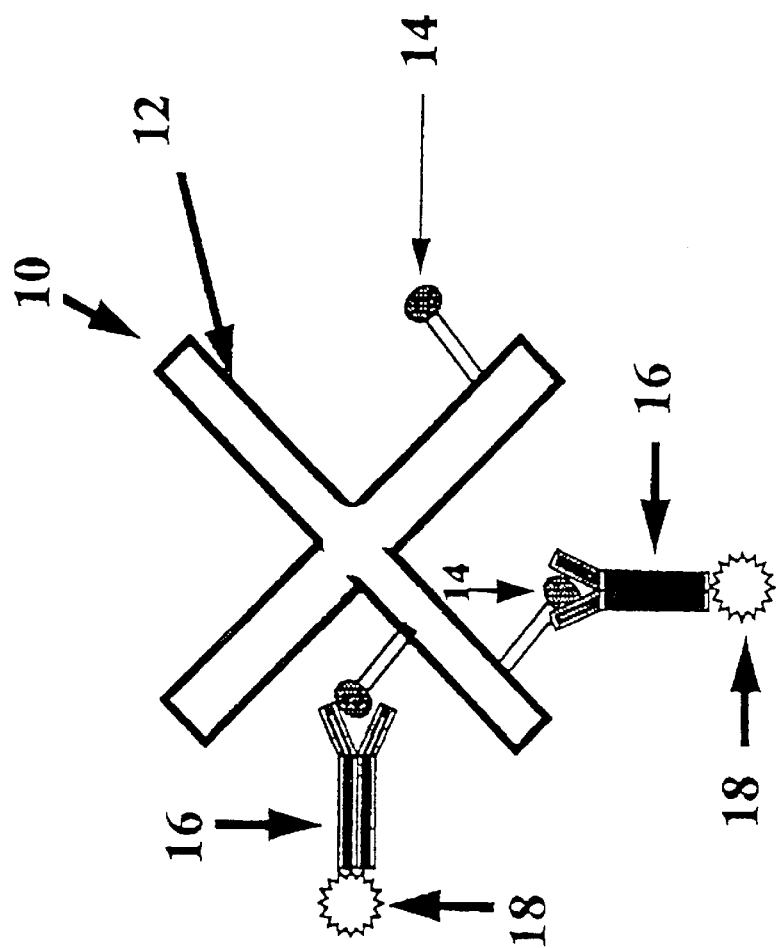

TARGETED RADIOIMMUNOTHERAPY

FIELD AND BACKGROUND OF THE INVENTION

The present invention relates to the targeting of radioactivity to a biomedical device and, in particular, to the use of radioimmunotherapy for the localization of radioactivity to stents for the reduction or elimination of restenosis.

Restenosis of blood vessels occurs after narrowed or occluded arteries are forcibly dilated by balloon catheters, drills, lasers and the like, in a procedure known as angioplasty. Such forcible dilation is required in order to reopen arteries which have been narrowed or occluded by atherosclerosis. However, up to 45% of all arteries which have been treated by angioplasty return to their narrowed state through the process of restenosis. Restenosis is caused both by recoil of the vessel wall towards its original dimensions and by neointimal hyperplasia induced by trauma to the vessel wall. Restenosis can significantly reduce the efficacy of angioplasty and as such is a major barrier to the effective treatment of narrowed arteries.

Attempts to reduce or eliminate restenosis have generally focused on the insertion of biomedical devices, such as stents, within the treated artery. Stents can reduce restenosis by preventing recoil of the treated blood vessel to its original dimensions. Various stents are known in the art, including coils and sleeves, those which are expandable by balloon catheters, heat expandable and self-expandable stents. Unfortunately, stents alone cannot prevent restenosis caused by neointimal hyperplasia of the tissues of the vessel wall. In fact, the stent material itself may accelerate such hyperplasia, since it is foreign to the body tissues.

Recently, as noted above, radionuclear irradiation of blood vessels has been proposed as a method of preventing restenosis caused by neointimal hyperplasia. The application of radionuclear irradiation to the body of a subject is a well accepted mode of therapy in medicine. The main use of such irradiation is for treating both malignant and benign tumors. Radionuclear irradiation can also be used to inhibit the undesired proliferation of cells in other rapidly growing tissues, such as keloids and blood vessels undergoing restenosis.

One study showed that such irradiation completely prevented restenosis of the treated arteries [H. D. Bottcher et al., *Int. J. Radiation Oncology Biol. Phys.*, 29:183–186, 1994]. A number of studies in animal models also support the efficacy of radionuclear irradiation of blood vessels for the prevention or reduction of restenosis following angioplasty [J. G. Wiedermann et al., *JACC*, 23:1491–8, 1994; R. Waksman et al., *Circulation*, 92:3025–3031, 1995; R. Waksman et al., *Circulation*, 91:1533–1539, 1995]. Thus, clearly exposing the walls of blood vessels to radioactivity is a valuable method of preventing and treating restenosis caused by neointimal hyperplasia.

Currently, radionuclear irradiation of blood vessels is performed by the insertion of temporary or permanent radionuclear sources into the vessels. For example, radioactive yttrium-90 wires were inserted into the central lumen of a balloon catheter in order to irradiate blood vessel walls [Y. Popowski et al., *Int. J. Radiation Oncology Biol. Phys.*, 43:211–215, 1995]. Other radioactive sources have included iridium-192, administered by catheter to arteries which had been treated by angioplasty [P. S. Teirstein et al., *Circulation*, 94:I-210, 1996]. U.S. Pat. No. 5,213,561 discloses a device for inserting a radionuclear source into a blood vessel, in which the source of radioactivity is mounted on a stent, for example.

Unfortunately, the insertion of radionuclear sources by a catheter or stent has a number of disadvantages. First, such procedures require a highly specialized clinical setting, which is appropriate both for catheterization procedures and for the handling of radioactivity. Second, these procedures are highly invasive. Third, temporary radioactive sources require repeated invasive treatments. However, temporary as well as permanent sources have the further disadvantage of decaying according to their specific half-life. Thus, current methods for irradiating blood vessels have significant disadvantages.

The concept of specifically targeting tumor cells is a goal of modern radio-oncology. The developing field of radiolabelled immunoglobulin therapy (RIT) employs radionuclide-labelled monoclonal antibodies which recognize tumor-associated antigens, thereby selectively targeting tumor cells. Beta particles emitted from a radiolabelled antibody bound to a tumor cell also kill neighboring cells because these particles can penetrate through several cell diameters. In B-cell lymphoma refractory to chemotherapy, RIT has been associated with a high rate of durable remissions [Kaminki et al., *JCO*, 14:1974–1981, 1996].

RIT may be effective for cancer treatment because tumor cells have special antigens on their surface, against which antibodies can be raised. Unfortunately, the situation is much more complicated for the prevention and treatment of restenosis. Restenotic tissue does not express special antigens, to that antibodies against such tissue would also bind to normal blood vessel walls and would not be sufficiently specific for the tissue to be treated. Thus, targeting antibodies directly to the tissue itself is not possible.

There is thus a widely recognized need for, and it would be highly advantageous to have, a method of targeting radioactivity to specific areas within a blood vessel or vessels, in order to perform localized radioimmunotherapy for treating or preventing restenosis of the vessel or vessels.

SUMMARY OF THE INVENTION

According to the teachings of the present invention, there is provided a biomedical device assembly for inhibition of tissue growth of a biological passageway, including: (a) a biomedical device for insertion into the biological passageway; and (b) an antigen for binding a labelled antibody, the antigen being attached to the biomedical device. Preferably, the biological passageway is a blood vessel. Also preferably, the antigen is a drug molecule. Preferably, the biomedical device is a stent. Preferably, the label is a radioactive source.

According to another embodiment of the present invention, there is provided a method of substantially inhibiting restenosis in a blood vessel of a subject, including the steps of. (a) inserting a stent into the blood vessel of the subject, the stent having an antigen attached; and (b) administering a labelled antibody to the subject, the antibody being capable of binding to the antigen. Preferably, the antibody has a radioactive source attached. Alternatively and preferably, the antibody has a pharmaceutically active moiety attached.

BRIEF DESCRIPTION OF THE DRAWINGS

The invention is herein described, by way of example only, with reference to the accompanying drawings, wherein:

FIG. 4 is a schematic representation of the stent of FIG. 1 with the antibody of FIG. 3.

DESCRIPTION OF THE PREFERRED EMBODIMENTS

The present invention is of a device and a method for localizing radioimmunotherapy to a biomedical device, such as a stent.

The principles and operation of such localized radioimmunotherapy according to the present invention may be better understood with reference to the drawings and the accompanying description. The following description is specifically directed toward localized radioimmunotherapy for a stent for purposes of clarity only, it being understood that many other biomedical devices could also be used. For example, artificial valves, coils or vascular grafts, or other implantable foreign bodies could also be used with the present invention. Also, the label on the antibody does not need to be a radioactive source, as described below.

Furthermore, although the term "antibody" is used to denote the molecule carrying the label, such as a radioactive source, and the term "antigen" is used for the molecule present on the biomedical device which is bound by the antibody, it is understood that any molecule which fulfills the function of the "antibody" or "antigen" could be used in their place.

Figure 1:
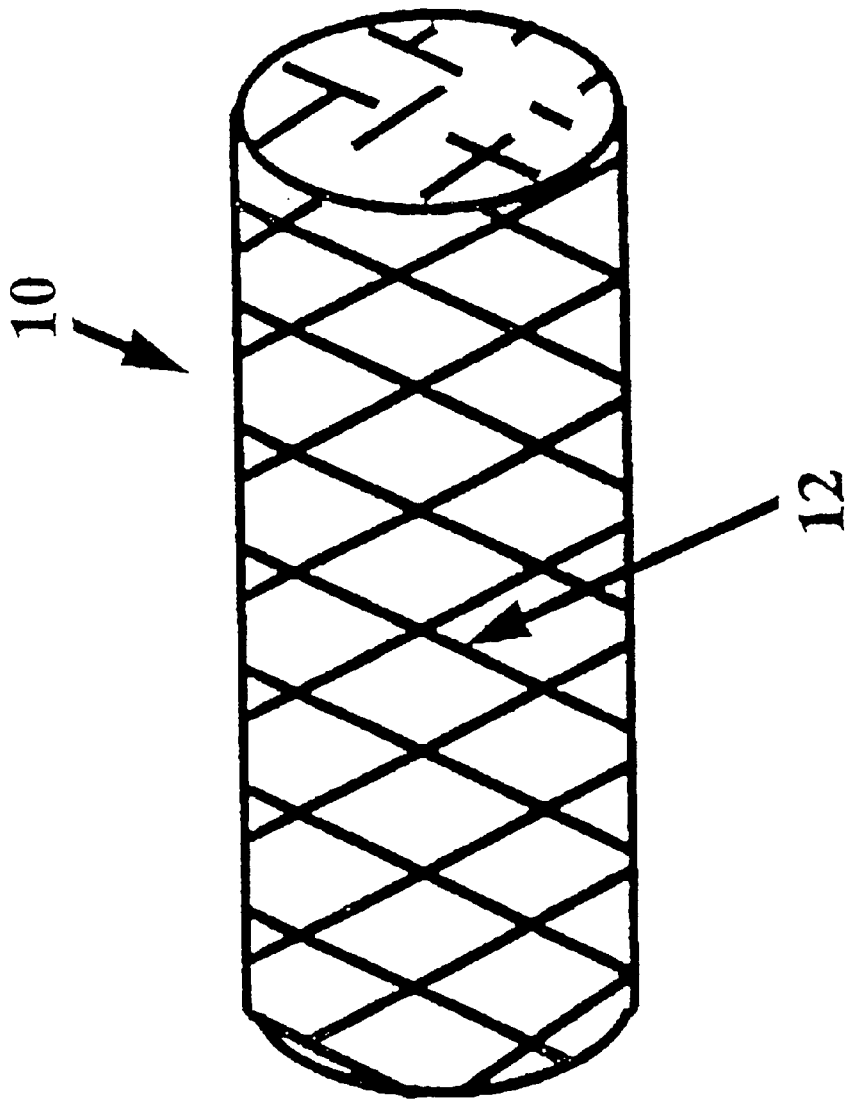
FIG. 1 is a schematic illustration of a stent according to the present invention.

Referring now to the drawings, FIG. 1 shows an expendable intraluminal stent 10 after deployment within a blood vessel (not shown). Stent 10 can be self-expandable, or inflated with a balloon catheter, for example. Stent 10 can be used for supporting collapsing vessel walls or for expanding partially occluded segments of a dilated blood vessel, catheter-created communication between portal and hepatic veins, narrowed esophagus, intestine, ureters, urethra, intracerebally, bile ducts, or any other duct or passageway in the human body, either in-born, built-in or artificially made.

Stent 10 is coated with a biocompatible material 12, such that biocompatible material 12 is attached to at least a portion of the surface of stent 10. Hereinafter, the term "attached" includes connected to, or integrally formed with. Biocompatible material 12 can be any material, such as Teflon or Dacron, which is suitable for insertion into the body of a subject. Such materials are well known in the art and could be selected by one of ordinary skill in the art. Hereinafter, the term "subject" refers to a human or other mammal on whom the method of the present invention is practiced.

Figure 2:
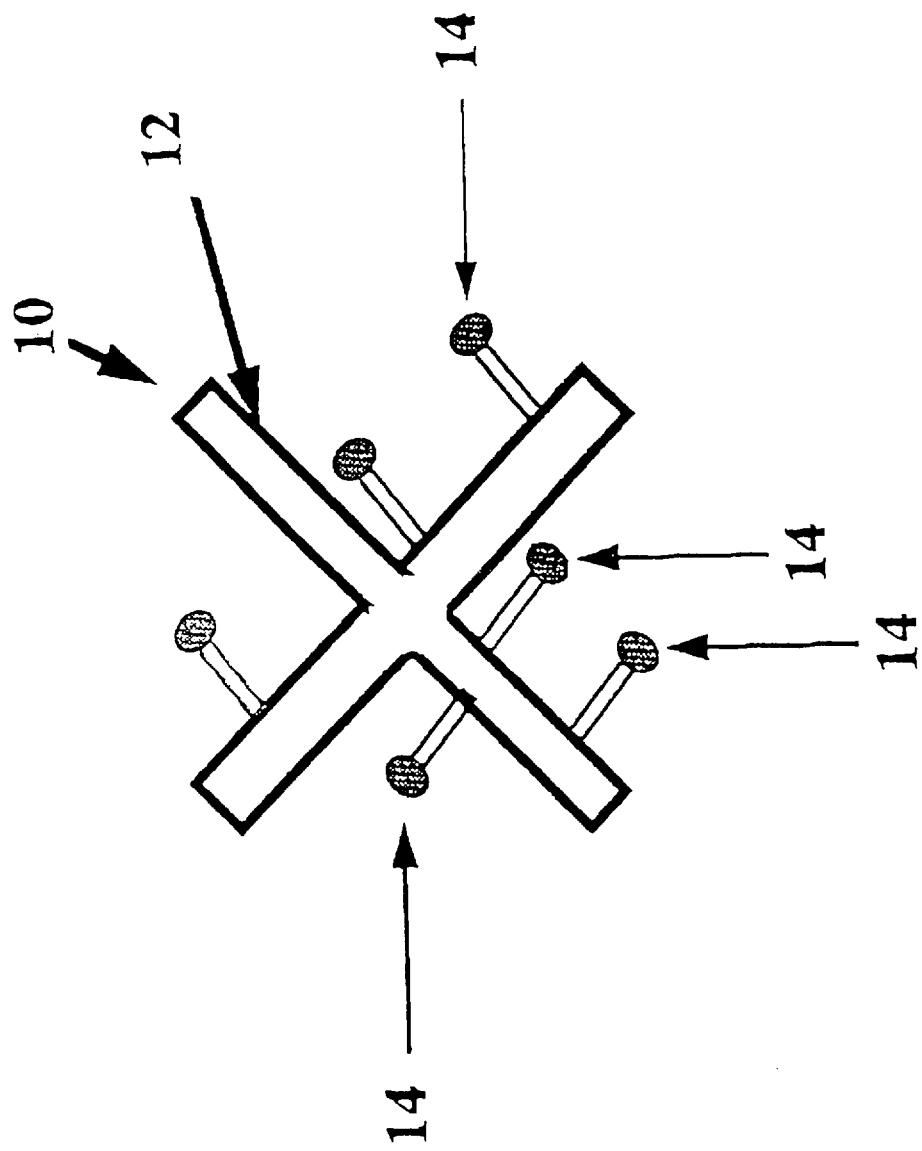
FIG. 2 is a schematic illustration of a portion of the stent of FIG. 1.

FIG. 2 shows a schematic magnification of a portion of the biocompatible material of FIG. 1. Biocompatible material 12 has at least one antigen 14 attached. As noted above, antigen 14 can be any molecule which is bindable by a second molecule, which can be an antibody, for example (not shown). Antigen 14 should not be a compound which already exists within the body, since this would prevent localization of an antibody to stent 10 (see below). Antigen 14 could be a pharmaceutical molecule such as an antibiotic, digoxin, cochicine and tricyclic antidepressants, for example. The advantage of using a known, clinically tested pharmaceutical molecule is that the safety of such a molecule will already have been extensively tested. Thus, the presence of such a molecule within the body of a subject would not be toxic in and of itself. Preferably, these molecules would not have any harmful effect on the blood vessel wall itself, although they could act to inhibit restenosis. Most preferably, these molecules would not have been administered to the subject during the implantation of stent 10, or for at least four weeks following the implantation of stent 10.

Preferably, antigen 14 is attached to biocompatible material 12 by a chemical reaction. For example, antigen 14 could be attached to biocompatible material 12 by co-incubation with a cross-linking reagent. Most preferably, such a chemical reaction would cause antigen 14 to be presented to the blood vessel for maximum recognition and binding by an antibody (not shown).

Figure 3:
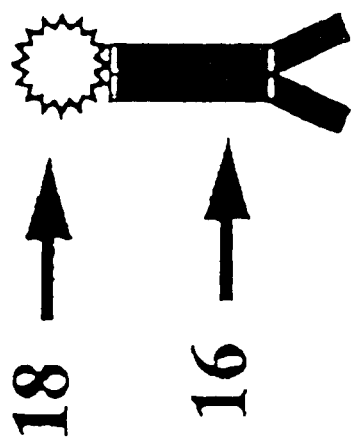
FIG. 3 is a schematic illustration of a portion of an antibody according to the present invention.
Figure 3:
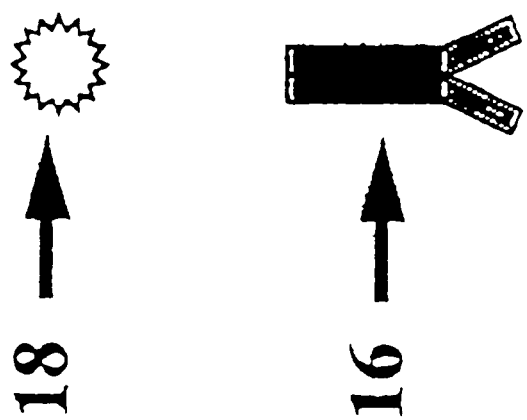

FIG. 3 is an illustration of a labelled antibody. An antibody 16 is shown, with a label 18 attached, and is designated as a "labelled antibody". Label 18 is preferably a radioactive source, which can be any suitable element for medicinal or therapeutic use which emits radioactivity, such as yttrium-90, iodine-132 or iridium-192, for example, and could be selected by someone of ordinary skill in the art. Label 18 could also, alternatively and preferably, be a pharmaceutical moiety, which is a composition used for medicinal or therapeutic purposes, such as an antibiotic, a chemotherapeutic agent, an enzyme, a growth factor, an inhibitor of an enzyme or an inhibitor of a growth factor, for example. Such a pharmaceutical moiety could be in the form of a slow-release formulation, for example. Such pharmaceutical moieties could easily be prepared by one of ordinary skill in the art.

As noted above, antibody 16 can be any molecule which is capable of binding to antigen 14 including, but not limited to, a substantially whole antibody, a fragment of an antibody such as a Fab, and an artificial molecule. By "artificial molecule", it is meant either a molecule which is at least partially synthesized in the laboratory, as well as a molecule which is designed for the specific purpose of carrying label 18.

The advantage of using a drug molecule for antigen 14 is that antibodies to many of these drugs are commercially available. Of course, new antibodies could be developed according to well known procedures in the prior art, if required.

FIG. 4 is an illustration of the stent after administration of the labelled antibody. Stent 10 has been placed in the blood vessel of a subject, as described for FIG. 1. Antibody 16 has been administered to the subject and is now bound to antigen 14 on biocompatible material 12. The combination of stent 10, antibody 16, antigen 14 and label 18 is an example of a "biomedical device assembly".

Antibody 16 is preferably administered parenterally, by intravenous injection for example, which is particularly preferable for administration to the genitourinary tract and to blood vessels, for example. Other examples of methods of administration include inhalation into an airway of the subject and oral administration to the gastrointestinal tract, for example. Since antibody 16 is labelled with label 18, the tissue of the blood vessel wall is now being specifically treated. For example, if label 18 is a radioactive source, the tissue is now being specifically irradiated. However, since antigen 14 is substantially only present on stent 10, substantially only the tissue of that portion of the blood vessel wall which is to be treated is being irradiated, in the case of a radioactive source for label 18. Thus, restenosis of the blood vessel is specifically inhibited, without exposing large areas of the body of a subject to radioactivity. Such specific inhibition could be used either for prevention or treatment, or both, of restenosis.

Furthermore, since stent 10 itself is not directly labelled, stent 10 can be implanted in the blood vessel of a subject according to any suitable catheterization procedure, which is well known in the art. Labelled antibody 16 can then be administered to the subject, at a later time and in a different location, if desired. Thus, stent 10 could be implanted in a standard catheterization laboratory, while antibody 16 could be administered in a standard radionuclear medicine laboratory, if label 18 is a radioactive source, for example. Also, catheterization time would not have to be prolonged in order to expose the blood vessels to the radioactive source, and the stents themselves would not require special handling.

Preferably, biocompatible material 12 has more than one type of antigen 14 attached, so that the treatment could be repeated more than once with different antibodies 16. Alternatively and preferably, different labels 18 could also be used in this embodiment, particularly for radioactive sources. The advantage of multiple treatments for such sources is that smaller, and therefore less toxic, amounts of radioactivity could be administered with each treatment. Furthermore, radioactive sources with different penetrating strengths could be used, allowing the sources to be tailored to the biological characteristics of the tissue to be treated. Preferably, antibody 16 could have one or more antigens attached (not shown) to which a second antibody could bind, either at substantially the same time or at a later time of administration. Such an arrangement would also facilitate multiple radioactive sources, or even a combination of one or more radioactive sources with another pharmaceutical moiety.

Thus, one example for using this embodiment of the biomedical device assembly would be to first insert stent 10 into a blood vessel of a subject, stent 10 having antigen 14 attached. Next, antibody 16 with label 18 could be administered to the subject. Such a method could be used for inhibiting restenosis in a subject. The term "inhibition" can include both prevention, substantially before restenosis has occurred, or treatment, substantially after restenosis has occurred, or both.

It will be appreciated that the above descriptions are intended only to serve as examples, and that many other embodiments are possible within the spirit and the scope of the present invention.

What is claimed is:

1. A biomedical device assembly comprising:
   a biomedical device, for insertion into a biological passageway, wherein said biomedical device comprises an antigen and an antibody having a label attached, wherein said antigen and said antibody are bound.

2. The biomedical device assembly of claim 1, wherein the biological passageway is selected from the group consisting of blood vessel, airway, gastrointestinal tract, intracerebal, bile duct and genitourinary tract.

3. The biomedical device assembly of claim 2, wherein the biological passageway is a blood vessel.

4. The biomedical device assembly of claim 1, wherein said antigen is a drug molecule.

5. The biomedical device assembly of claim 1, wherein said biomedical device is selected from the group consisting of coil, artificial valve, vascular graft and stent.

6. The biomedical device assembly of claim 5, wherein said biomedical device is a stent.

7. The biomedical device assembly of claim 1, wherein said label is selected from the group consisting of radioactive source and pharmaceutical moiety.

8. The biomedical device assembly of claim 7, wherein said label is a radioactive source.

9. A method of substantially inhibiting restenosis in a blood vessel of a subject, comprising the steps of:
   (a) inserting a stent into the blood vessel of the subject, said stent having an antigen attached; and
   (b) administering an antibody to the subject, said antibody being capable of binding to said antigen and said antibody having a label attached wherein said label is capable of inhibiting restenosis.

10. The method of claim 9, wherein said label is selected from the group consisting of radioactive source and pharmaceutical moiety.

11. The method of claim 10, wherein said label is a radioactive source.

\* \* \* \* \*